United States Patent [19]

Patel et al.

[11] Patent Number: 5,449,685
[45] Date of Patent: Sep. 12, 1995

[54] METHOD AND COMPOSITION FOR TREATING HIV-TYPE 1 INFECTIONS

[75] Inventors: Mahesh G. Patel, Verona; Vincent P. Gullo, Liberty Corner, both of N.J.; Jerome Schwartz, New York, N.Y.

[73] Assignee: Schering Corporation, Kenilworth, N.J.

[21] Appl. No.: 966,125

[22] Filed: Oct. 23, 1992

Related U.S. Application Data

[63] Continuation of Ser. No. 809,024, Dec. 16, 1991, abandoned, and a continuation of Ser. No. 537,177, Jun. 13, 1990, abandoned.

[51] Int. Cl.$^6$ .......................................... A61K 31/335
[52] U.S. Cl. ................................................... 514/475
[58] Field of Search ........................................ 514/475

[56] References Cited

U.S. PATENT DOCUMENTS 3,257,161 6/1966 Kaye ........................................ 21/58
3,400,200 9/1968 Fan et al. ............................... 424/283

FOREIGN PATENT DOCUMENTS 400646 12/1969 Japan ............................ A01N 9/20

OTHER PUBLICATIONS

Pauwels et al., Nature, (1 Feb. 1990), vol. 343, 470–474.
Weislow et al., Journal of the National Cancer Institute, (Apr. 19, 1989), vol. 81, (No. 8), p. 577.
McMahon et al., Antimicrobial Agents and Chems. Therapy, (Apr. 1993), vol. 37, (No. 4), pp. 754–760.
Holland, et al., AIDS Research and Human Retrovirus, (1992), vol. 8, (No. 9), pp. 1717–1722.
Buckhert et al., Antiviral Research, (1993), vol. 21, pp. 247–265.
R. Cooper et al., The J. of Antibiotics, (1988), vol. 41, (No. 1), pp. 13–19.
D. Baltimore et al., New England Journal of Medicine, (1989), vol. 321, (No. 24), 1673-75.
R. Andruszkiewicz et al., The J. of Antibiotics, (1984), vol. 37, (No. 11), pp. 1479–1482.
J. March, Advanced Organic Chem., (1968), pp. 578–579 and 618–621.
R. W. Coombs et al., N. Engl. J. Med., (1989), vol. 321, (#24), pp. 1626'1631.
D. Ho et al., N. Engl. J. Med., (1989), vol. 321, (No. 24), pp. 1621–1625.
J. L. Fahey, N. Engl. J. Med., (1990), vol. 321, (No. 3), pp. 166–172.
J. B. Jackson et al., N. Engl. J. Med., (1990), vol. 322, (No. 4), pp. 217–222.

*Primary Examiner*—Marianne M. Cintins
*Assistant Examiner*—Russell Travers
*Attorney, Agent, or Firm*—Thomas D. Hoffman

[57] ABSTRACT

A method of treating mammals infected with HIV-1, or AIDS by administering a therapeutically effective amount of a compound represented by formula I $$\underset{1}{CH_3}-\underset{2}{\underset{|}{\overset{NH_2}{C}}H}-\underset{3}{\overset{O}{\overset{\|}{C}}}-\underset{4}{NH}-\underset{5}{\underset{|}{\overset{CO_2H}{C}}H}-\underset{6}{CH_2}-\underset{7}{NH}-\underset{8}{\overset{O}{\overset{\|}{C}}}-\underset{9\;10}{\overset{O}{\overset{/\;\backslash}{CH-CH}}}-\underset{11}{\overset{O}{\overset{\|}{C}}}-\underset{12}{NH_2}$$

or a pharmaceutically acceptable salt or ester thereof or stereoisomer thereof and pharmaceutical compositions containing it are disclosed.

7 Claims, 1 Drawing Sheet

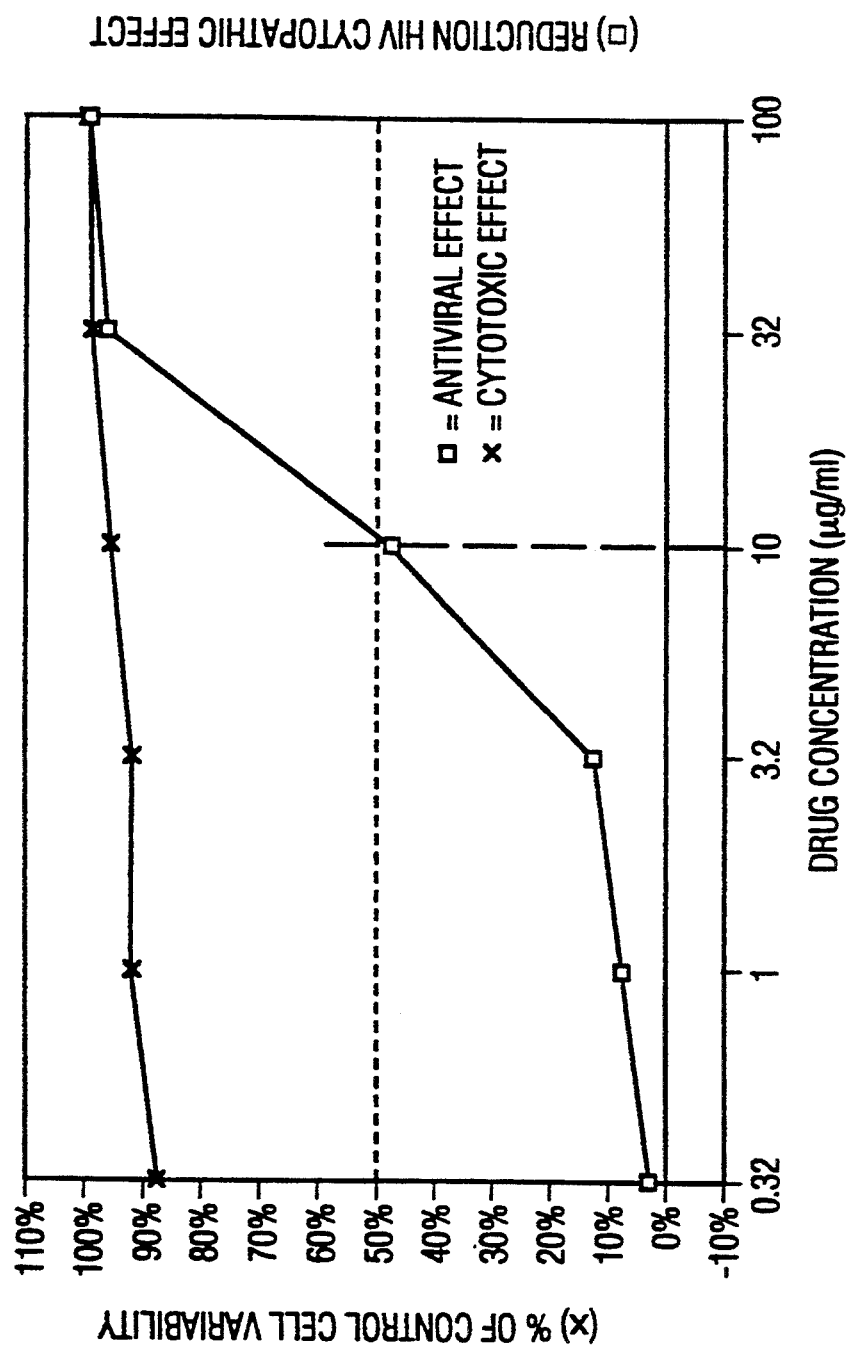
FIGURE

METHOD AND COMPOSITION FOR TREATING HIV-TYPE 1 INFECTIONS

This is a continuation of application Ser. No. 07/809,024, now abandoned, filed Dec. 16, 1991 and Ser. No. 07/537,177, now abandoned filed Jun. 13, 1990.

BACKGROUND OF THE INVENTION

This invention is directed to a method of treating a mammal infected with human immunodeficiency virus type 1, which comprises administering to such mammals a therapeutically effective amount of a dipeptide compound represented by the formula I

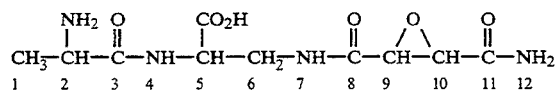

or a pharmaceutically acceptable salt or ester thereof or a stereochemical isomer thereof.

The dipeptide compound of formula I is disclosed by R. Cooper et al. in *The Journal of Antibiotics*, 1988, Vol. 41 (No. 1 ), pp 13-19, to be an antifungal compound which was produced by fermentation of the microorganism Micromonospora sp.

The human immunodeficiency virus type 1 ("HIV-1") is now generally considered to be the, cause of acquired immunodeficiency syndrome ("AIDS"). See the editorial by D. Baltimore and M. B. Feinberg in *The New England Journal of Medicine*, 1989, Vol. 321 (No. 24), pp 1673-1675. The human immunodeficiency virus type 2 ("HIV-2") is a cause of AIDS in West Africa.

People infected with HIV-1, HIV-2, AIDS and AIDS-Related Complex ("ARC") are being treated with various anti-HIV agents such as zidovudine (AZT), 2'-3'-dideoxycytidine (DDC), 2',3'-dideoxyinosine (DDI) and certain tetrahydro-imidazo[4,5,1-jk][1,4]-benzodiazepin-2(1H)-one and -thione ("TIBO") derivatives. However, the AZT, DDC and DDI anti-HIV agents are relative highly cytotoxic to human lymphocytes uninfected by HIV-1 (i.e., have a relatively low margin of safety). The synthesis of the TIBO compounds are complex, time-consuming and provide only small amounts of these compounds.

There is still a need for an anti-HIV-1 agent which is not highly cytotoxic and can be synthesized simply and in high yield.

SUMMARY OF THE INVENTION

The present invention provides a method of treating a mammal infected with human immunodeficiency virus type 1 which comprises administering to said mammal a therapeutically effective amount of a compound represented by the formula I:

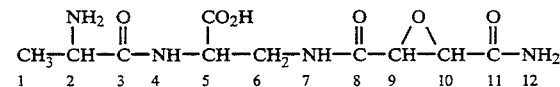

or a pharmaceutically acceptable salt or ester thereof or a stereochemical isomer thereof.

The present invention further provides a method of treating a mammal infected with acquired immune deficiency syndrome caused by human immunodeficiency virus type 1 which comprises administering to said mammal a therapeutically effective amount of a compound represented by the formula I

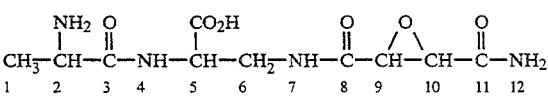

or a pharmaceutically acceptable salt or ester thereof or a stereochemical isomer thereof.

The present invention also provides a pharmaceutical composition for treating a mammal infected with human immunodeficiency virus type 1, acquired immunodeficiency syndrome or acquired immunodeficiency syndrome-related complex comprising a therapeutically effective amount of a compound represented by formula I, together with a pharmaceutically acceptabler carrier therefor wherein the human immunodeficiency virus is implicated as the cause of said syndrome and complex.

BRIEF DESCRIPTION OF THE FIGURE

The sole Figure graphically illustrates the selective antiviral activity of a preferred embodiment of this invention.

DETAILED DESCRIPTION OF THE INVENTION AND OF THE PREFERRED EMBODIMENTS

The compound found useful in the method of this invention is represented by formula I

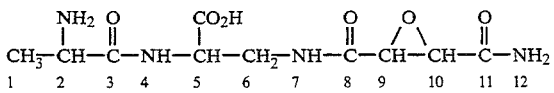

including the pharmaceutically acceptable salts and esters thereof as well as the stereochemical isomers thereof.

The compounds of formula I may form pharmaceutically acceptable acids such as hydrochloric, hydrobromic, methanesulfonic, toluenesulfonic, sulfuric or nitric or trihaloacetic acids, e.g. trichloroacetic and trifluoroacetic acids. The compounds of this invention of formula I also may form salts by reaction of the carboxylic acid novelty at C-5 with pharmaceutically acceptable bases such as the hydroxides of the alkali metal (especially Li, Na or K), the alkaline earth (esp Ca, Mg and Sr) or ammonium hydroxides. Pharmaceutically acceptable esters of compounds of formula I may be include $C_1$-$C_6$ lower alkyl especially methyl and ethyl as well as p-nitrobenzyl, indanyl, phthalidyl, methoxymethyl, glycloxymethyl, phenylglycyloxymethyl, thienylglycyloxymethyl, acetoxymethyl and pivaloyloxymethyl.

The compound represented by formula I includes stereo isomers due to the presence of two asymetric carbon atoms (C-2 and C-5) and geometric isomerism at (C$_9$ and C$_{10}$. All stereoisomers of formula I are contemplated as part of this invention.

In a preferred aspect of the method of the present invention, it is preferred to use the stereoisomers of the compund of formula I having the formula II:

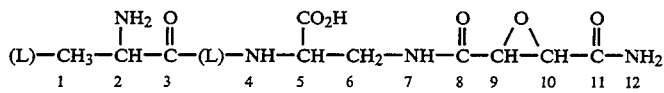

wherein the L indicates that L enantiomers of alanine and of 2,3-diaminopropanoic acid and the hydrogens attached to C-9 and C-10 are trans relative to each other.

The preferred stereoisomers of the compounds of formula I are represented by Formula II and are isolated from an antimicrobial (anti viral) complex produced by cultivating a strain of Micromonospora sp SCC 2217 having the identifying characteristics of ATCC 55064 in a pH and temperature controlled aqueous nutrient medium containing assimilable sources of nitrogen and carbon, under controlled submerged aerobic conditions, until a composition of matter having substantial antimicrobial activity is produced.

A variable culture of the Micromonospora sp SCC 2217 ATCC 55064 was deposited on Jun. 12, 1990 with The American Type Culture Collection, 12301 Parklawn Drive, Rockville Md. 20852 U.S.A.

The stereoisomers represented by formula II may also be prepared by epoxidation of $N^2$-L-alanyl-$N^3$-fumaramoyl-L-2,3-diaminopropionic acid which has been prepared by R. Andruszkiewicz et al [*The Journal of Antibiotics* (1984). Vol 37 (No. 11) pp 1479–1482]. Suitable epoxidation reagents include peroxy acids such as peracetic and pertrichloroacetic acids, meta-chloroperoxybenzoic acid as well as those disclosed by J. March in "Advanced Organic Chemistry", McGraw-Hill, 1968, N.Y., at pp 578–579 and 618–621.

The racemic mixture or D-enantiomer of compounds represented by formula I may be prepared by substitution in the procedure of R. Andruszkiewic supra of racemic or D-alanine for L-alanine, respectively, and of racemic or D-2,3-diaminopropionic acid for the L-enantiomer thereof and of maleamic acid, respectively, for the fumaramic acid.

Antiviral Activity

A sample of the compound represented by Formula II was tested in vitro for activity against the HIV-IIIb strain of HIV-1 growing in MT-2 cells, a human lymphocyte derived cell line in accordance with the procedure disclosed by P. Daniels et al. in Antiviral Research SI (1990), 1–130 (Elsevier, Science Publishers B.V.) (0166-3542/90).

The sample was tested at a single concentration (1:20 dilution of the submitted broth), in duplicate on HIV-1 infected MT-2 cells to measure antiviral efficacy and at the same concentration on uninfected MT-2 cells to measure the cytotoxic effect of the product. Assays were set up in 96-well plates, the sample was tested and three replicates of virus control cultures (untreated, infected cells) and three replicates of cell control cultures (untreated, uninfected cells) were used. A panel of control cultures (AZT and DDC at various concentrations; alone and in combination with the sample) were set up with each test. Assay end-points were read at Day 7 post-infection by MTT, a formazan-activating tetrazolium salt used to measure cell viabilities (Tata, et al, *J. Immunol Methods*, 93:157–165). Criteria for selection of active compounds included arbitrary limits of 49% or less viability of test sample=inactive; 50–74% viability=marginally active; and 75–100%=active. Active and marginally active compounds were re-tested to confirm activity. Compounds meeting criteria of active are undergoing further in vitro activity and cytotoxicity testing.

The compound represented by Formula II reduces the cytopathy (CPE) caused by HIV-IIIb strain of HIV-1 by 50% at a concentration of 10 μg/m L. The % CPE reduction for the HIV-infected MT-2 cells is defined by the relationship:

$$\% \ CPE = \frac{[\text{Mean Infected Cells} - \text{Mean Virus Control}] \times 100\%}{[\text{Mean Cell Control} - \text{Mean Virus Control}]}$$

FIG. 1 graphically illustrates the in-vitro activity of the compound represented by formula II.

The sole Figure graphically displays the in vitro activity of the preferred compound represented by formula II against MT-2 cells infected with the HIV-IIIb strain of HIV as well as the against the uninfected MT-2 cells at the six concentration of such preferred compound of 0.32, 1,3.2, 10, 32 and 100 μg/mL (noted on the horizontal axis of FIG. 1 ). The reduction in the cytopathology (CPE) opf the HIV-IIIb infected MT-2 cells, i.e. the antiviral activity, of the stereoisomer of the compound represented by formula II at the six concentrations is plotted versus the right vertical axis to give the curve defined by the data points in the form of boxes. The viability of cells uninfected by the HIV-IIIb strain at the same six contrations is plotted versus the left vertical axis to give the upper curve defined by the data points in the form of X's.

At concentrations of the compound represented by formula II as high as 100 μg/mL, the uninfected MT-2 tissue culture cell remained 100% viable. Thus, the selectively index for the compound represented by formula II is at least 10 or more, i.e., the compound represented by formula II inhibits HIV-1 replication at concentraiton at least 10 times below the levels at which the viability of uninfected human lymphocyte cells are impaired. This assay is predictive of clinical utility in mammals infected with AIDS. See R. Pauwels et al. *Nature* (1990), Vol. 343, p 470–474.

The methods and pharmaceutical compositions of the present invention are useful for treating mammals infected with the human immunodeficiency virus Type 1. The progression of HIV-1 in mammals, especially male and female human beings has been separated into roughly three stages: (1) the early or acute phase, lasting weeks; (2) the middle or chronic phase, lasting and characterized by minimal but measurable pathologic changes; and the final or crisis phase generally referred to as the AIDS-related complex (ARC) or AIDS and lasting months to years depending on the effacy and availabilty of treatment. The mammals to be treated for the HIV-1 infection or AIDS or ARC in accordance with the present invention complete standardized questionnaires about the signs and symptoms of HIV infection, and are given a complete physical examination and are classified according to their stage of disease caused by HIV-1 as defined by the Centers for Disease Control, *MMWR* (1986), Vol. 35, Suppl. 15, pp. 334-9 and MMWR (1987), Vol. 36, Suppl. 15, pp. 35–155. The progress of the HIV-1 infection and the evaluation of responses to treatment in accordance with this invention may be determined by measurement of frequency of isolation of HIV-1 in peripheral-blood mononuclear cells (PBMC) and the frequency of isolation of HIV-1 from cell-free plasma (plasma viremia) (3) the presence and titer of p24 antigen in plasma and (4) the presence and filter of antibody to p24 antigen in accordance with the methods disclosed by R. W. Coombs et al., N. Engl. J Med. (1989), Vol. 321 (No. 24), pp 1626–1631 and Dr. D. Ho et al., ibid (1989), Vol. 321 (No. 24), pp 1621–1625. Ho et al. and Coombs et al. disclose that the increasing levels of HIV-1 in plasma viremia provides a good indication of the clinical status of a mammal infected with HIV-1 and provides support for early treatment of the infection. The prognostic value of three cellular (the number of CD4+T cells, the number of CD8+T cells and the ratio of CD4+T cells to CD8 T cells) and five serologic markers (serum levels of neopterin—a product of stimulated macrophages), beta$_2$-microglobulin, soluble interleukin-2 receptors, IgA and HIV p24 antigen with HIV-1 as well as the methods of measuring all eight markers are disclosed by J. L. Fahey et al. in the N. Engl. J. Med. (1990), Vol. 322 (No. 3), p 166–17. J. L. Fahey et al. disclose that the progression to AIDS was predicted in mammals infected with HIV-1 most accurately by the level of CD4+T cells in combination with the serum level of teither neopterin or beta$_2$-microglobulin. At least one of the aforesaid serum markers, which reflect immune activation, should be used along with measurement of CD4+T cells in HIV-1 cause disease classification schemes and in the evaluation of the response to treatments in accordance with the present invention.

The presence of HIV-1 in mammals to be treated in accordance with the present invention may also be determined in apparently healthy persons by use of test of blood thereof for HIV-1 antibody by two different enzyme immunoassays and a Western blot assay, as disclosed by J. B. Jackson et al. in the N. Engl. J. Med. (1990), Vol. 322 (No. 4), pp 217–222.

The "therapeutically effective amount" of a pharmaceutical acceptable salt or ester or stereoisomer of a compound represented by formula I is in a dosage range of about 1 to about 100 mg/kg (body weight) per day with 1 to about 10 mg per day being preferred.

The precise amount of a composition containing a compound represented by formula I or salt or ester or stereoisomer thereof would be determined by the attending clinicians taking into account the etiology and severity of the disease, the patients' condition, sex and age and other factors.

The compounds represented by formula I or salts or esters or stereoisomers thereof and the pharmaceutical compositions of the present invention may be administered by parenteral, oral, systemic or topical means.

The compound represented by formula I or a pharmaceutically acceptable salt or ester or stereoisomer thereof may be compounded into a dosage form suitable for oral or parenteral administration. A tablet or capsule or caplets are particularly convenient forms for oral administration. Such compositions useful in the present invention are typically formulated with conventional pharmaceutical excipients, e.g., spray dried lactose and magnesium stearate into tablets or capsules for oral administration. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as a magensium stearate, sodium lauryl sulfate, "Carbowax" or polyethylene glycols. Of course, taste improving substances can be added in the case of oral administration forms.

As further forms of administration, one can use plug capsules, e.g. hard gelatin, as well as closed soft gelatin capsules comprising a softner or plasticizer, e.g., glycedne. The plug capsules contain the active substance preferably in the form of a granulate, e.g., in mixtures with fillers, such as lactose, saccharose, mannitol, starches such as potato starch or amylopectin, cellulose derivatives or highly-dispersed silicic acids. In soft-gelatin capsules, the active substance is preferably dissolved or suspended in suitable liquids, such as vegetable oils or liquid polyethylene glycols.

The compounds represented by formula I used in accordance with the present invention may also be formulated into once-a-day or even longer sustained release composition by conventional techniques well known in the art.

In place of oral administration, the compounds represented by formula I may be administered parenterally. In such case, one can use a solutin of the active substance, e.g., in sesame oil or olive oil.

EXAMPLE 1 a) FERMENTATION

The culture of Micromonospora sp SCC 2217, ATCC 55064 was stored as a stock suspension at −20° C. in a growth medium containing 12% (w/v) sucrose solution. Three mL of a thawed suspension was used to inoculate 70 mL of growth medium consisting of the following ingredients listed in concentrations expressed as percent (%) by weight per unit volume: beef extract 0.3% (w/v), tryptone 0.5%, yeast extract 0.5%, cerelose 0.1%, potato starch 2.4%, CaCO$_3$ 0.2% and Dow-Corning antifoam-B 0.1%, in a 250-mL Erlenmeyer flask. After 48 hours incubation at 30° C. on a rotary shaker operating at 300 rpm, 25 mL of the resulting cell suspension was used to inoculate 500 ml of the growth medium in a 2-liter Erlenmeyer flask. The culture was incubated as described above. After 48 hours, the entire contents of the flask were used to inoculate 10 liters of fermentation medium consisting of NZ-amine A 0.5%, yeast extract 0.5%, cerelose 1.0%, soluble starch 2.0%, CaCO$_3$ 0.4%, COCl$_2$ 0.0004% and Dow-Corning antifoam-B 0.1% in a 14-liter fermentor (New Brunswick Scientific, Edison, N.J.). The fermentation was carried out at 30° C. with aeration of 3.5 liters/minute and agitation of 350 rpm. The pH and dissolved oxygen levels were continuously monitored without adjustment during the entire fermentation by means of probes submerged in the vessel. Microbial growth was determined by packed cell volume. The antibiotic production started 48 hours after inoculation, then gradually increased reaching a maximum at 96 hours. The amount of antibiotic produced was determined by a paper-disk agar diffusion method using Candida albicans strain 406 as the test organism.

b) ISOLATION AND PURIFICATION OF THE COMPOUND REPRESENTED BY FORMULA II

The compound represented by formula II was recovered from 110 liters (pH 7) of fermentation broth filtrate obtained in accordance with the procedure Example 1 (a) of by absorption thereof on the cation exchange BioRad AG 50×8 (H+). Elution with 2 liters of 0.5N NH4OH provided a filtrate which was concentrated to give 78.8 g of eluate. The concentrated eluant was absorbed onto BioRad AG 1×8 (HCO3−) and eluted with CO2-saturated water. The eluant was lyophilized and the resultant solid (3.4 g) was subjected to chromatography on charcoal and elution with 1 liter gradient 0 to 20% aq. MeOH to provide 1.3 g of a white amorphous solid having the following physico-chemical properties:

Physico-Chemical Properties of the Compound Represented by Formula II

Amphoteric, water soluble compound, MP 198° C. (dec) $[\alpha]^{26}{}_D -30.6°$ (c.0.5, H2O)
Stable at RT in the pH 2 to 9 range.
FAB Mass Spectra Data:
  MW: 288 amu
  M+H: m/z 289 (found 289.1163, calc. 289.1148) corresponding to the molecular formula $C_{10}H_{17}N_4O_6$.
UVλ (max) (H2O): no absorbance maxima greater than 215 nm.
IR (KBr): 3300 cm−1 (br, NH, and OH) and 1650 cm−1 (amide).
13C NMR showed the presence of 10 carbon atoms including four carbonyls; the two carbon signals at 54.2 and 54.6 ppm were assigned to the epoxide carbons. i.e. C-9 and C-10 in formula II.
1H NMR spectrum in D2O was also consistent with the presence of an epoxide and two epoxide protons having the trans configuration relative to each other on the basis of the small coupling constant.

Acid hydrolysis of the white amorphous solid of Example 1b gave L-alanine and L-2,3-diaminopropanoic acid. The above physico-chemical data and the pH-dependent 1H NMR chemical shift study is consistent with the structure shown by formula II. [See R. Cooper et al., *The Journal of Antibiotic* Vol. 41 (No. 1), pp 13–19.]

What is claimed is:

1. A method of treating human immunodeficiency virus type 1 infection which comprises administering to a mammal suffering therefrom a therapeutically effective amount of a compound represented by the formula I:

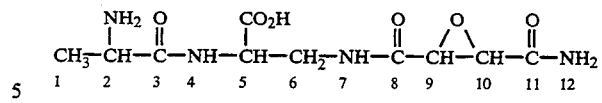

or a pharmaceutically acceptable salt or ester thereof or a stereochemical isomer thereof.

2. The method of claim 1 wherein the stereoisomer of the compound represented by formula I is

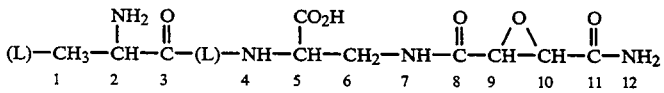

and wherein the hydrogen atoms attached to the C-9 and C-10 carbon atoms have the trans configuration relative to each other.

3. The method of claim 1 wherein the compound represented by formula I is isolated from an antimicrobial (antiviral) complex produced by cultivating a strain of Micromonospora sp SCC 2217 having the identifying characteristics of ATCC 55064 in a pH and temperature controlled aqueous nutrient medium containing assimilable sources of nitrogen and carbon, under controlled submerged aerobic conditions, until a composition of matter having substantial antimicrobial activity is produced.

4. The method of claim 1 wherein in the compound represented by formula I the hydrogen atoms on carbon atoms 9 and 10 have the trans configuration relative to one another.

5. A method of treating acquired immune deficiency syndrome caused by human immunodeficiency virus type 1 infection which comprises administering to a mammal suffering therefrom a therapeutically effective amount of a compound represented by the formula I

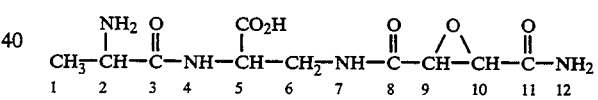

or a pharmaceutically acceptable salt or ester thereof or a stereochemical isomer thereof.

6. The method of claim 5 wherein the stereoisomer of the compound represented by formula I is

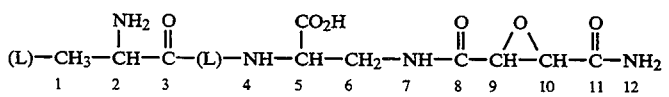

and wherein the hydrogen atoms on the carbon atoms 9 and 10 have trans configurate relative to each other.

7. The method of claim 5 wherein the compound represented by formula I is isolated from an antimicrobial (antiviral) complex produced by cultivating a strain of Micromonospora sp SCC 2217 having the identifying characteristics of ATCC 55064 in a pH and temperature controlled aqueous nutrient medium containing assimilable sources of nitrogen and carbon, under controlled submerged aerobic conditions, until a composition of matter having substantial antimicrobial activity is produced.

* * * * *